United States Patent [19]

Tsuchida et al.

[11] Patent Number: 4,656,135

[45] Date of Patent: Apr. 7, 1987

[54] PROCESS FOR PRODUCING L-ISOLEUCINE BY FERMENTATION

[75] Inventors: Takayasu Tsuchida, Tokohoma; Noboru Otsuka; Hiroshi Sonoda, both of Yokohama, all of Japan

[73] Assignee: Ajinomoto Co., Inc., Tokyo, Japan

[21] Appl. No.: 750,289

[22] Filed: Jul. 1, 1985

[30] Foreign Application Priority Data

Jun. 29, 1984 [JP] Japan ................................. 59-134460
Jun. 29, 1984 [JP] Japan ................................. 59-134461

[51] Int. Cl.$^4$ ............................................. C12P 13/06
[52] U.S. Cl. ................................... 435/116; 435/840
[58] Field of Search ............................... 435/116, 840

[56] References Cited

U.S. PATENT DOCUMENTS 3,943,038  3/1976  Morinaga et al. ................. 435/116
4,237,228  12/1980 Zhdanova et al. ................. 435/116
4,329,427  5/1982  Updike et al. ..................... 435/116
4,442,208  4/1984  Tsucheda et al. ................. 435/116

*Primary Examiner*—Blondel Hazel
*Attorney, Agent, or Firm*—Oblon, Fisher, Spivak, McClelland & Maier

[57] ABSTRACT

A process for producing L-isoleucine, which comprises culturing a microorganism belonging to the genus Brevibacterium or the genus Corynebacterium which has a methyllysine resistance or α-ketomalonic acid resistance and which is capable of producing L-isoleucine in a liquid medium, and obtaining the accumulated L-isoleucine from said medium.

8 Claims, No Drawings

PROCESS FOR PRODUCING L-ISOLEUCINE BY FERMENTATION

BACKGROUND OF TH INVENTION

1. Field of the Invention

L-Isoleucine is an important component for parenteral and enteral nutrition and complex amino acid preparations. The present invention involves an improvement to a process for producing L-isoleucine by fermentation.

2. Description of the Prior Art

It is known that in order to impart L-isoleucine productivity to microorganisms belonging to the genus Brevibacterium or the genus Corynebacterium, it may be sufficient for the microorganisms to have resIstances to α-amino-β-hydroxyvaleric acid (hereafter simply referred to as AHV), etc. (Published Examined Japanese Patent Application No. 20316/73, U.S. Pat. No. 3,767,529). It is also known that the productivity of L-isoleucine may be improved by imparting to the microorganisms, in addition to the above-mentioned chemical resistances, O-methylthreonine resistance, β-hydroxyleucine resistance or trichloroalanine resistance, and by imparting thereto auxotrophy for purine type substances or lysine, etc. (Published Examined Japanese Patent Applications Nos. 21077/76, 4629/77, 29998/81 and 3035/81, and Published Unexamined Japanese Patent Application No. 2687/82).

From a viewpoint of industrial production, it is of importance to improve the fermentation yield or accumulation of L-isoleucine.

SUMMARY OF THE INVENTION

The present invention has been made to solve the foregoing problem. As a result of investigations on hitherto known microorganisms belonging to the genus Brevibacterium or the genus Corynebacterium and having L-isoleucine productivity with an attempt to improve these microorganisms and to find strains providing improved fermentation yields, it has been found that among those strains having imparted thereto resistance to methyllysine (hereafter simply referred to as ML) or a α-ketomalonic acid (hereafter simply referred to as α-KM), are found strains having L-isoleucine productivity in a higher yield than with known L-isoleucine-producing bacteria.

That is, the present invention relates to a process for producing L-isoleucine, which comprises culturing a microorganism belonging to the genus Brevibacterium or the genus Corynebacterium, having ML resistance or α-KM resistance and capable of producing L-isoleucine in a liquid medium and obtaining the accumulated L-isoleucine from said medium.

DESCRIPTION OF PREFERRED EMBODIMENTS

Examples of ML's of the present invention include methyllysines such γ-ML, β-ML, δ-ML, ε-ML, etc. Bacteria having resistance thereto are effective for improving L-isoleucine productivity.

The microorganisms used in the present invention are mutants which belong to the genus Brevibacterium or the genus Corynebacterium, possess ML resistance or α-KM resistance and are capable of producing L-isoleucine.

To obtain the mutants of the present invention, wild strains described below may first have imparted thereto L-isoleucine productivity and then have imparted thereto ML resistance or α-KM resistance; alternatively, ML resistance or α-KM resistance may be first imparted to the wild strains followed by having L-isoleucine productivity imparted thereto.

Examples of the wild strains that are parent strains of the mutants are known as Coryneform L-glutamic acid-producing bacteria belonging to the genus Brevibacterium or the genus Corynebacterium, examples of which are shown below.

*Brevibacterium lactofermentum* ATCC 13869
*Brevibacterium divaricatum* ATCC 14020
*Brevibacterium saccarolyticum* ATCC 14066
*Brevibacterium flavum* ATCC 14067
*Corynebacterium glutamicum* ATCC 13032
*Corynebacterium acetoamidophilum* ATCC 13870.

To obtain the mutants of the present invention from these parent strains, a conventional process for mutation and induction, such as by treating the parent strains with N-methyl-N'-nitro-N-nitrosoguanidine, etc. is applicable. Separation of the mutants of the present invention from the bacterial solution obtained by mutation treatment may be carried out by collecting strains that grow on a medium containing ML or α-KM.

The relationship between a specific process for mutation of the mutants of the present invention and the degree of growth of strains in the presence of γ-ML or α-KM is shown below.

Process for mutation

*Brevlbacterium flavum* AJ 3686 FERM-P 2433, FERM-BP 755 (AHV resistant strain induced from ATCC 14067) and *Corytnebacterium glutamicum* AJ 12150 FERM-P 7674, FERM-BP 756 (AHV resistant strain induced from ATCC 13032) were grown on bouillon agar slant at 30° C. for 24 hours. The thus grown cells were suspended in M/30 phosphate buffer to a cell concentration of $10^8$ to $10^9$/ml. To the cell suspensions, 500 μg/ml of N-methyl-N'-nitro-N-nitrosoguanidine was added and the mixture was maintained at 30° C. for 20 minutes. Then, the system was centrifuged to collect the bacteria. After the bacteria were thoroughly washed with M/30 phosphate buffer, the bacteria were inoculated on medium having the composition shown in Table 1, and were cultured at 31.5° C. for 2 to 10 days.

TABLE 1

| Composition of Medium | |
|---|---|
| Component | Content |
| Glucose | 1.0 g/dl |
| Urea | 0.2 g/dl |
| KH$_2$PO$_4$ | 0.1 g/dl |
| MgSO$_4$.7H$_2$O | 0.1 g/dl |
| FeSO$_4$.7H$_2$O | 0.002 g/dl |
| MnSO$_4$.7H$_2$O | 0.002 g/dl |
| Biotin | 100 μg/l |
| Thiamine hydrochloride | 100 μg/l |
| γ-ML or α-KM | 0.2 g/dl |
| Agar | 2.0 g/dl |

From the bacteria that grew in agar medium containing γ-ML, *Brevibacterium flavum* AJ 12149 FERM-P 7677, FERM-BP 759 (AHV resistance, γ-methyllysine resistance) and *Corynebacterium glutamicum* AJ 121251 FERM-p 7675, FERM-BP 757 (AHV resistance, γ-methyllysine resistance) were selected as having high productivity of L-isoleucine.

Further, from the strains that grew in agar medium containing α-KM, *Brevibacterium flavum* AJ 12152, FERM-P 7678, FERM-BP 760 (AHV resistance, α-KM resistance) and *Corynebacterium glutamicum* AJ 12153, FERM-P 7676, FERM-BP 758 (AHV resistance, α-KM resistance) were obtained as strains having high productivity of L-isoleucine.

The strain FERM-P was originally deposited on Jan. 8, 1974 and the strains FERM-P 7674, FERM-P 7675, FERM-P 7676, FERM-P 7677 and FERM-P 7678 were deposited on June 22, 1984 at the Fermentation Research Institute, Agency of Industrial Sciences and Technology, Ministry of International Trade and Industry (FRI), 1-3, Migashi 1-chome, Yatabe-machi, Tsukuba-gun, Ibaragi-ken 305, Japan. These deposited strains were then converted into deposits under the Budapest Treaty on Apr. 10, 1985, and were accorded the corresponding FERM-BP numbers.

The degree of γ-ML resistance or the degree of α-KM resistance of the thus obtained variants was compared with that of the parent strains.

The bacteria obtained by culturing in natural medium (1 g/dl peptone, 1 g/dl yeast extract, 0.5 g/dl NaCl, pH 7.0) slant for 24 hours were suspended in sterilized water. The suspension was inoculated on medium containing 0.5 g/dl glucose, 0.2 g/dl urea, 0.15 g/dl ammonium sulfate, 0.3 g/dl $KH_2PO_4$, 0.1 g/dl $K_2HPO_4$, 0.01 g/dl $MgSO_4 \cdot 7H_2O$, 0.1 mg/dl $CaCl_2 \cdot 2H_2O$, 100 μg/l biotin, 100 μg/l thiamine hydrochloride, 0.002 g/dl $FeSO_4 \cdot 7H_2O$, and γ-ML or α-ML in the amount shown in Table 2, the pH of which was adjusted to 7.0. After culturing for 24 hours, the degree of growth was determined by turbidity.

above-mentioned auxotrophy, and if necessary, vitamins and other organic trace nutrients.

As carbon sources, carbohydrates such as glucose, sucrose, etc., organic acids such as acetic acid, etc. are preferred and as nitrogen sources, ammonia water, ammonia gas, ammonium salts, etc. are preferred. If necessary, potassium ions, sodium ions, magnesium ions, phosphate ions and others are appropriately added to the medium as inorganic ions.

It is preferred that the cultivation be conducted under aerobic conditions. When the cultivation is carried out while adjusting the pH of the medium to 4 to 8 and the temperature to 25° to 37° C. during the cultivation, more preferred results are obtained. Cultivation for 1 to 7 days under the conditions produces and accumulates marked amounts of L-isoleucine. L-isoleucine may be harvested from the culture solution in a conventional manner such as using ion exchange resins, etc.

The invention now being generally described, the same will be better understood by reference to the following examples which are included herein for purposes of illustration only and are not intended to be limiting of the invention or any embodiment thereof, unless specified.

EXAMPLES

A medium containing 10 g/dl glucose, 7 g/dl $(NH_4)_2SO_4$, 0.1 g/dl $KH_2PO_4$, 0.04 g/dl $MgSO_4 \cdot 7H_2O$, 1 mg/dl $FeSO_4 \cdot 7H_2O$, 1 mg/dl $MnSO_4 \cdot 4H_2O$, $CaCl_2 \cdot 2H_2O$, 100 μg/l thiamine hydrochloride, 100 μg/l biotin, 60 mg/dl (as the total nitrogen) soybean protein acid hydrolysate solution and 5 g/dl calcium carbonate (separately sterilized) was adjusted to a pH of 7.0, 20 ml of

TABLE 2

| Strain | Concentration of γ-ML (g/dl) | | | | | Concentration of α-KM (g/dl) | | | | |
|---|---|---|---|---|---|---|---|---|---|---|
| | 0 | 0.05 | 0.1 | 0.2 | 0.3 | 0 | 0.05 | 0.1 | 0.2 | 0.3 |
| | Degree of Growth (%) | | | | | | | | | |
| *Brevibacterium flavum* AJ 3686 FERM-P 2433 FERM-BP 755 | 100 | 90 | 58 | 20 | 0 | 100 | 90 | 45 | 0 | 0 |
| *Brevibacterium flavum* AJ 12149 FERM-P 7677 FERM-BP | 100 | 90 | 90 | 85 | 80 | — | — | — | — | — |
| *Brevibacterium flavum* AJ 12152 FERM-P 7678 FERM-BP 760 | — | — | — | — | — | 100 | 100 | 95 | 95 | 80 |
| *Corynebacterium glutamicum* AJ 12150 FERM-P 7674 FERM-BP 756 | 100 | 88 | 75 | 30 | 0 | 100 | 95 | 50 | 0 | 0 |
| *Corynebacterium glutamicum* AJ 121251 FERM-P 7675 FERM-BP 757 | 100 | 88 | 85 | 85 | 82 | — | — | — | — | — |
| *Corynebacterium glutamicum* AJ 12153 FERM-P 7676 FERM-BP 758 | — | — | — | — | — | 100 | 100 | 90 | 90 | 85 |

In most cases, the yield can be further improved by additionally imparting to the aforesaid mutants a property that is already known to improve the productivity of L-isoleucine, such as O-methylthreonine resistance, β-hydroxyisoleucine resistance or trichloroalanine resistance.

The medium used for culturing such mutants is a conventional one containing carbon sources, nitrogen sources, inorganic ions, substances for satisfying the which was charged in a 500 ml volume-flask followed by thermal sterilization. A platinum loop of the strain shown in Table 1 was inoculated on the medium. While being maintained at 31° C., the system was shaken for 4 days. In the culture solution of each strain, L-isoleucine was accumulated in the amount shown in Table 3. AJ 12149 was cultured in a similar manner to obtain 1 liter of the culture solution. From the culture solution, the bacteria were removed by centrifugation and the supernatant was passed through a strongly acidic ion exchange resin "Diaion" SK-1B (NH+ type). After rinsing the resin with water, elution was conducted with ammonia water. Then the eluate was concentrated and from the concentrate, 17.0 g of crude L-isoleucine crystals were obtained.

TABLE 3

| Strain | Property | Amount of L-isoleucine accumulated (g/dl) |
| --- | --- | --- |
| Brevibacterium flavum AJ 3686 FERM-P 2433 FERM-BP 755 | AHV$^r$ | 0.6 |
| Brevibacterium flavum AJ 12149 FERM-P 7677 FERM-BP 759 | AHV$^r$, γ-ML$^r$ | 1.9 |
| Brevibacterium flavum AJ 12152 FERM-P 7678 FERM-BP 760 | AHV$^r$, α-KM$^r$ | 1.8 |
| Corynebacterium glutamicum AJ 12150 FERM-P 7674 FERM-BP 756 | AHV$^r$ | 0.5 |
| Corynebacterium glutamicum AJ 12151 FERM-P 7675 FERM-BP 757 | AHV$^r$, γ-ML$^r$ | 1.7 |
| Corynebactium glutamicum AJ 12153 FERM-P 7676 FERM-BP 758 | AHV$^r$, α-KM$^r$ | 1.6 |

What is claimed as new and desired to be secured by Letters Patent of the United States is:

1. A process for producing L-isoleucine, which comprises culturing a microorganism belonging to a genus selected from the group consisting of Brevibacterium and Corynebacterium, wherein said microorganism has a resistance to lysine substituted with a methyl group in the β, δ, γ, or ε position or α-ketomalonic acid resistance and wherein said microorganism is also capable of producing L-isoleucine in a liquid medium, and obtaining accumulated L-isoleucine from said medium.

2. The process of claim 1, wherein said culturing is carried out while adjusting the pH of said medium to from 4 to 8 at a temperature of from about 25° to 37° C. for from 1 to 7 days.

3. The process of claim 1, wherein said microorganism having a resistance to lysine substituted with a methyl group in the β, δ, γ, or ε position or α-ketomelonic acid resistance is produced by mutation of a parent strain selected from the group consisting of Brevibacterium lactofermentum ATCC 13869
Brevibacterium divaricatum ATCC 14020
Brevibacterium saccarolyticum ATCC 14066
Brevibacterium flavum ATCC 14067
Corynebacterium glutamicum ATCC 13032
Corynebacterium acetoamidophilum ATCC 13870.

4. The process of claim 1, wherein said microorganism which is resistant to lysine substituted by a methyl group at the β, δ, γ, or ε position or α-ketomalonic acid is produced by treating a parent microorganism belonging to a genus selected from the group consisting of Brevibacterium and Corynebacterium which is not resistant to lysine substituted by a methyl group at the β, δ, γ, or ε position or α-ketomalonic acid with N-methyl-N'-nitro-N-nitrosoguanidine.

5. The process of claim 1, wherein said microorganism is Brevibacterium flavum AJ 12149, FERM-P 7677, FERM-BP 759.

6. The process of claim 1, wherein said microorganism is Corynebacterium glutamicum AJ 121251, FERM-P 7675, FERM-BP 757.

7. The process of claim 1, wherein said microorganism is Brevibacterium flavum AJ 12152, FERM-P 7678, FERM-BP 760.

8. The process of claim 1, wherein said microorganism is Corynebacterium glutamicum AJ 12153, FERM-P 7676, FERM-BP 758.

* * * * *